United States Patent
Kriz

(10) Patent No.: US 7,910,063 B2
(45) Date of Patent: Mar. 22, 2011

(54) DRIFT COMPENSATED MAGNETIC PERMEABILITY DETECTOR

(75) Inventor: Dario Kriz, Höör (SE)

(73) Assignee: Lifeassays AB, Lund (SE)

( * ) Notice: Subject to any disclaimer, the term of this patent is extended or adjusted under 35 U.S.C. 154(b) by 1928 days.

(21) Appl. No.: 10/506,768

(22) PCT Filed: Mar. 7, 2003

(86) PCT No.: PCT/SE03/00360
§ 371 (c)(1),
(2), (4) Date: Sep. 7, 2004

(87) PCT Pub. No.: WO03/076931
PCT Pub. Date: Sep. 18, 2003

(65) Prior Publication Data
US 2005/0093535 A1 May 5, 2005

(30) Foreign Application Priority Data
Mar. 8, 2002 (SE) ...................... 0200705

(51) Int. Cl.
*B01L 3/00* (2006.01)
*G01N 25/18* (2006.01)
*G01N 27/00* (2006.01)
*G01N 33/553* (2006.01)

(52) U.S. Cl. ............ 422/82.01; 422/68.1; 422/102; 422/104; 435/4; 435/5; 435/6; 435/7.1; 435/7.2; 435/7.21; 435/7.22; 435/7.31; 435/7.32; 435/287.2; 435/525; 435/526; 435/149

(58) Field of Classification Search .............. None
See application file for complete search history.

(56) References Cited

U.S. PATENT DOCUMENTS

| 4,357,237 | A  | * | 11/1982 | Sanderson ............... 210/222 |
| 5,025,656 | A  |   | 6/1991  | Wright |
| 5,978,694 | A  |   | 11/1999 | Rapoport |
| 6,110,660 | A  |   | 8/2000  | Kriz et al. |
| 2002/0012916 | A1 | * | 1/2002 | Gundling et al. .......... 435/6 |
| 2003/0111312 | A1 | * | 6/2003 | Stretch ................. 192/21.5 |

FOREIGN PATENT DOCUMENTS

| EP | 1 146 347  | 10/2001 |
| JP | 62-147357  | 7/1987 |
| JP | 06-317639  | 11/1994 |
| JP | 08-220072  | 8/1996 |
| JP | 09-133652  | 5/1997 |

OTHER PUBLICATIONS

C.B. Kriz, "Magnetic Permeability Measurements in Bioanalysis and Biosensors", Anal. Chem., 68, No. 11, pp. 1966 to 1970 (1966). K. Kriz et al., "Advancements toward magneto immunoassays", Biosensors & Bioelectronics, No. 13, pp. 817 to 823 (1998).
K. Larsson et al., "Magnetic Tranducers Biosensors and Bioassays", Analusis, Vo. 27, No. 7, pp. 617 to 621 (1999).
Notice of Allowance from Korean Intellectual Property Office in corresponding Korean Patent Application No. 10-2004-7013998, dated Nov. 12, 2010.

* cited by examiner

*Primary Examiner* — Unsu Jung
(74) *Attorney, Agent, or Firm* — Buchanan Ingersoll & Rooney PC

(57) ABSTRACT

A device for detection of magnetic permeability $\mu$ or, alternatively, relative magnetic permeability $\mu_r$ or, alternatively, relative magnetic susceptibility $(\mu_r-1)$ of a sample, wherein said device contains a sample chamber and at least two coils, one coil surrounding said sample chamber and one coil placed so as to be in thermal contact by being physically connected to the material which constitutes the sample chamber, but without surrounding the cavity of the sample chamber, said sample chamber having at least one opening for introduction of a sample or a sample container holding a sample, said device also provided with an electronic circuit which measures the difference in inductance between the two coils.

17 Claims, 2 Drawing Sheets

US 7,910,063 B2

DRIFT COMPENSATED MAGNETIC PERMEABILITY DETECTOR

CROSS-REFERENCE TO RELATED APPLICATIONS

This application is a National Stage application of PCT/SE03/00360 filed on Mar. 7, 2003, which claim priority to Swedish application no. 0200705-2, filed on Mar. 8, 2002.

FIELD OF THE INVENTION

The present invention relates to a device for use when measuring magnetic permeability ($\mu$) or, alternatively, relative magnetic permeability ($\mu_r$).

BACKGROUND ART

The annual world market for diagnostic equipment based on immunoassays has increased considerably in the last few decades. The main reason for the success of immunoassays is that the method is general and easy to adjust to various chemical analysis problems. By using different types of detection techniques in combination with immunoassays, a number of important chemical substances can be identified and quantified. Depending on the physical measuring principle, different types of detectors are suitable for different types of analysis problems. Since the introduction of immunoassays, a great deal of detectors with excellent performance have been presented. One type of detector uses magnetic permeability as the basis for detection. Such a detector, which is described in SE 9502902-1 and U.S. Pat. No. 6,110,660, allows quick and simple identification of substances using immunoassay technology. The measurements are carried out by placing samples in a measuring coil whose inductance is measured and compared with a separate air-filled reference coil. This type of device allows measuring of magnetic permeability of samples, but it suffers from the drawback that the temperature-dependent drift limits the sensitivity of the detector. The temperature drift is caused by variations in the temperature of the sample and by the fact that the temperature of, respectively, the measuring coil and the reference coil is affected differently by the actual measuring process.

The present invention solves the problem of temperature-dependent drift in a new and efficient manner when measuring magnetic permeability or, alternatively, relative magnetic permeability. Furthermore, it makes it possible to obtain other parameters from the collected measuring data, which parameters are connected to magnetic permeability, for example magnetic susceptibility.

Magnetic immunoassays are based on the principle that a sample is introduced into a sample container, containing one or more magnetic reagents and a liquid, and then the sample container is placed in an instrument for reading the concentration of an analyte. (Kriz et al., Analytical Chemistry 68, p 1966 (1996); Kriz et al., Biosensors & Bioelectronics 13, p 817 (1998); Larsson K. et al., Analysis 27, p 78, 1999).

The above-mentioned documents, SE 9502902-1, U.S. Pat. No. 6,110,660 and Larsson K. et al., Analysis 27, p 78, 1999, disclose prior-art devices and methods, in which use is made of detection of magnetic permeability for quantitative chemical analyses of samples placed in a measuring coil. Said devices and methods do not, however, comprise an integrated double coil, i.e. a measuring coil and a reference coil which simultaneously surround a sample container. Consequently, there is no continuous temperature drift compensation, which means that the temperature of the sample has to be kept constant. It is difficult in practice, and in some cases even impossible, to control the temperature of the sample during the measuring process, in particular when it is placed in the measuring coil during the actual measuring process.

Other prior-art techniques also comprise a flow detector for liquid chromatography based on measurements of Nuclear Magnetic Resonance, NMR (Spraul M. et al., NMR Biomed 7, 295-303, 1994). However, this detector does not measure the magnetic permeability which, unlike NMR, is a macroscopic property originating from the outside of the atomic nucleus in a material. In addition, this device does not comprise a double coil as in the present invention.

SUMMARY OF THE INVENTION

The present invention thus relates to a device, which is characterised in that it contains a sample chamber which is surrounded by at least two coils, which are connected to an electric circuit that measures the difference in inductance between the coils, said device being capable of analysing qualitatively and quantitatively the contents of chemical substances in a sample container placed in said sample chamber or, alternatively, determining the magnetic permeability of a substance placed in the sample container.

The present invention further relates to a device for detection of magnetic permeability $\mu$ or alternatively, relative magnetic permeability $\mu_r$ or, alternatively, relative magnetic susceptibility ($\mu_r$-1) of a sample, wherein the device contains a sample chamber and at least two coils, one coil surrounding the sample chamber and one coil being placed so as to be in thermal contact by being physically connected to the material which constitutes the sample chamber, but without surrounding the cavity of the sample chamber. The sample chamber has at least one opening for introduction of a sample or a sample container holding a sample. The device is also provided with an electric circuit, which measures the difference in inductance between the two coils.

The invention also relates to a method in which a device according to the invention is used for detection of various chemical substances in a sample container and which is not limited to immunoassays such as, for example, affinity bindings or synthetic peptide-based bindings selected from phage libraries. Furthermore, the invention relates to a method in which a device according to the invention is used in particular as a blood analysis instrument for clinical use (e.g. for determining blood gases, electrolytes, trace metals, Hb, glucose, protein markers, complement factors, hormones, bacteria, viruses, yeast, cells, fungi, spores, phages, cell or ganelles, DNA and RNA).

DETAILED DESCRIPTION OF THE INVENTION

According to one aspect of the invention, the device is characterised in that said coils have a self-inductance in the range of 0.01 to 100 µH.

According to another aspect, the device is characterised in that said sample chamber has a chamber volume in the range of 0.1 to 5000 µl.

According to an aspect of the invention, the device is characterized in that the material of which the sample chamber is made is a polymer, such as DELRIN (acetal resin), POM (polyoxymethylene), polyvinyl chloride, TEFLON (polytetrafluoroethylene), polyamide, polyacetal, polyethylene, polycarbonate, polystyrene, and polypropylene, wood, glass, or a metal with $0.999 < \mu_r > 1.001$.

Figure 2:
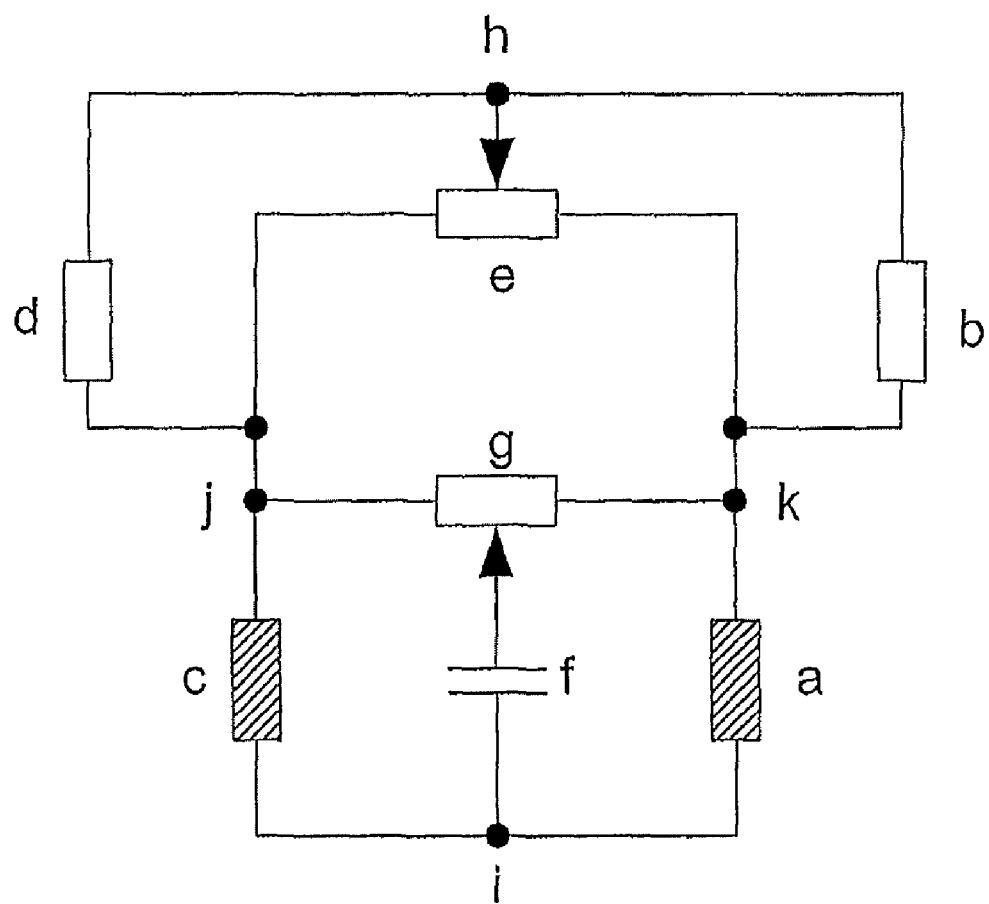
FIG. 2 shows an example of an electronic circuit.

According to a further aspect, the device is characterised in that it contains an electronic circuit according to FIG. 2.

According to yet another aspect, the device is characterised in that it is provided with an electronic circuit whose output signal is proportional to the difference in inductance between said coils and to the relative magnetic permeability ($\mu_r$) of the sample introduced into the sample chamber, which is in the range of $0.0000001 < \mu_r < 5$.

According to another aspect, the device is characterised in that it is provided with an electronic circuit which is formed such that said measuring coil is part of an alternating current bridge.

According to another aspect, the device is characterised in that it is provided with two or more double coil systems for simultaneous detection of several samples.

According to another aspect, the device is characterised in that it is provided with more than two coils which surround the sample chamber to carry out measurements at different locations in the same sample or in different sediment layers in the sample container.

According to still another aspect, the device according to the invention is characterised in that it is provided with complementary prior-art physical techniques of measurement for determining light absorbency, light emission, dissolved gas, ion content and electric conductivity.

Chemical substances with high magnetic permeability can be identified directly or used as specific reagents in diagnostic applications.

Figure 1:
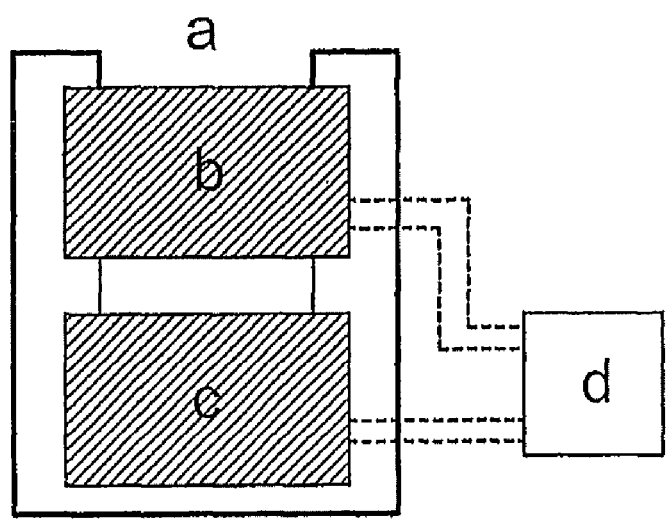
FIG. 1 is a basic diagram showing the principle of the device according to the present invention.

FIG. 1 shows a basic diagram illustrating the underlying principle of the present invention. An opening (a) to the sample chamber makes it possible to introduce a sample container with various chemical substances (a). The sample chamber is surrounded by a reference coil (b) and a measuring coil (c), the inductance of the coils being affected by the introduced sample. The sample, which is assumed to have a homogenous temperature, affects the two coils equally. A solution, a solid sample or a sediment with an enriched magnetic marker at the bottom of the sample container affects the inductance in the measuring coil (c) of the double coil without affecting the reference coil. A signal is thus obtained whose magnitude has been compensated for temperature variations so that the difference in inductance between the coils can be measured more precisely. The device can advantageously comprise an electronic circuit according to FIG. 2 so as to obtain an electric output signal.

FIG. 2 shows an example of an electronic circuit. The measuring coil (a) with an inductance of 9 μH (0.3 mm copper wire, 30 turns, D=8 mm) is connected in series with a 10 ohm resistor (b). The reference coil (c) with an inductance of. 9 μH (0.3 mm copper wire, 30 turns, D=8 mm) is connected in series with a 10 ohm resistor (d). Via the resistors (b) and (d), a 50 ohm trimming potentiometer (e) with 10 turns is connected. Via the coils (a) and (c), a 10 nF capacitor (f) and a 500 ohm trimming potentiometer (g) are connected. The electronic circuit is supplied with alternating voltage (2 V pp, 200 kHz, sinus) through the points. (h) and (i). By adjusting the trimming potentiometers (e) and (g), the amplitude and phase of the circuit are balanced. The electric signal generated between the points (j) and (k) are, when introducing chemical substances with high magnetic permeability into the flow-through chamber, proportional to the change in the inductance of the measuring coil, which in turn is proportional to the concentration of said chemical substances.

The device according to the invention can advantageously be used for detection, on the one hand, of chemical substances with high magnetic permeability and, on the other hand, of chemical substances with $\mu_r=1$, for example, haemoglobin, complement factors, proteins, hormones, bacteria, cells, viruses, fungi, yeast, spores, phages, cell organelles, DNA, RNA, which require interaction with magnetic markers, which makes the present device unique. Irrespective of purpose, the method can be carried out under conditions with varying sample temperature, which reduces the temperature-caused drift.

The invention claimed is:

1. A device for detection of magnetic permeability μ or, alternatively, relative magnetic permeability $\mu_r$ or, alternatively, relative magnetic susceptibility ($\mu_r-1$) of a sample, wherein said device contains a sample chamber and at least two coils, one coil surrounding said sample chamber and one coil placed so as to be in thermal contact by being physically connected to the material which constitutes the sample chamber, but without surrounding the cavity of the sample chamber, said sample chamber having at least one opening for introduction of a sample or a sample container holding a sample, said device also provided with an electronic circuit which measures the difference in inductance between the two coils.

2. The device as claimed in claim 1, wherein each of said coils, when filled with air, has an inductance in the range of 0.01 to 100 μH.

3. The device as claimed in claim 1, wherein said sample chamber has a chamber volume in the range of 0.1 to 5000 μl.

4. The device as claimed in claim 1, wherein the material of which the sample chamber is made is a polymer, wood, glass, or a metal with $0.999 < \mu_r > 1.001$.

5. The device as claimed in claim 1, wherein it is provided with an electronic circuit whose output signal is proportional to the difference in inductance between said coils and to the relative magnetic permeability of the sample material placed in one of the coils, which is in the range of $0.0000001 < \mu_r < 10$.

6. The device as claimed in claim 5, wherein said electronic circuit is formed such that said coils are part of an alternating current bridge.

7. The device as claimed in claim 2, wherein said sample chamber has a chamber volume in the range of 0.1 to 5000 μl.

8. The device as claimed in claim 2, wherein the material of which the sample chamber is made is a polymer, wood, glass, or a metal with $0.999 < \mu_r > 1.001$.

9. The device as claimed in claim 3, wherein the material of which the sample chamber is made is a polymer, wood, glass, or a metal with $0.999 < \mu_r > 1.001$.

10. A device as claimed in claim 2, wherein it is provided with an electronic circuit whose output signal is proportional to the difference in inductance between said coils and to the relative magnetic permeability of the sample material placed in one of the coils, which is in the range of $0.0000001 < \mu_r < 10$.

11. The device as claimed in claim 3, wherein it is provided with an electronic circuit whose output signal is proportional to the difference in inductance between said coils and to the relative magnetic permeability of the sample material placed in one of the coils, which is in the range of $0.0000001 < \mu_r < 10$.

12. A device as claimed in claim 4, wherein it is provided with an electronic circuit whose output signal is proportional to the difference in inductance between said coils and to the relative magnetic permeability of the sample material placed in one of the coils, which is in the range of $0.0000001 < \mu_r < 10$.

13. The device as claimed in claim 8, wherein the polymer material of which the sample chamber is made is selected from the group consisting of acetal resin, polvoxvmethylene, polyvinyl chloride, polytetrafluoroethylene, polyamide, polyacetal, polyethylene, polycarbonate, polystyrene, and polypropylene.

14. The device as claimed in claim 8, wherein the polymer material of which the sample chamber is made is selected from the group consisting of acetal resin, polvoxvmethylene, polyvinyl chloride, polytetrafluoroethylene, polyamide, polyacetal, polyethylene, polycarbonate, polystyrene, and polypropylene.

15. The device as claimed in claim 9, wherein the polymer material of which the sample chamber is made is selected from the group consisting of acetal resin, polyoxymethylene, polyvinyl chloride, polytetrafluoroethylene, polyamide, polyacetal, polyethylene, polycarbonate, polystyrene, and polypropylene.

16. A process for interaction with magnetic markers, for detection of chemical substances with $\mu_r = 1$, comprising the utilization of the device of claim 1.

17. A process for interaction with magnetic markers, for detection of chemical substances with $\mu_r = 1$, comprising the utilization of the device of claim 2 to detect chemical substances selected from the group consisting of proteins, hormones, complement factors, bacteria, cells, viruses, fungi, yeast, spores, phages, cells, cell organelles, DNA, and RNA.

* * * * *